United States Patent [19]

Powell

[11] 4,257,958
[45] Mar. 24, 1981

[54] STABILIZED ACID ANHYDRIDES

[75] Inventor: Justin C. Powell, Wappingers Falls, N.Y.

[73] Assignee: Texaco Inc., White Plains, N.Y.

[21] Appl. No.: 42,684

[22] Filed: May 25, 1979

[51] Int. Cl.$^3$ ............... C07D 307/58; C07D 307/89; C07D 309/32
[52] U.S. Cl. ................ 260/346.7; 260/333; 260/345.2; 260/345.7 R; 260/346.3; 260/346.74; 260/346.76
[58] Field of Search .......... 260/346.7, 346.74, 346.76, 260/346.3, 345.2, 345.7, 333

[56] References Cited

U.S. PATENT DOCUMENTS

| | | | |
|---|---|---|---|
| 2,850,440 | 9/1958 | Shrader et al. | 260/346.7 X |
| 3,328,429 | 6/1967 | Meinstein et al. | 260/346.7 X |
| 3,939,183 | 2/1976 | Gardner et al. | 260/346.7 X |

Primary Examiner—Richard Raymond
Attorney, Agent, or Firm—Carl G. Ries; Robert A. Kulason; Carl G. Seutter

[57] ABSTRACT

Acid anhydrides such as maleic anhydride are stabilized against the deteriorative effects of heat by addition thereto of an inorganic boron-oxygen compound typified by boric acid, boric anhydride, tributly borate, or borax.

22 Claims, No Drawings

STABILIZED ACID ANHYDRIDES

FIELD OF THE INVENTION

This invention relates to novel anhydrides of polycarboxylic acids which have been stabilized against the deteriorative effect of heat.

BACKGROUND OF THE INVENTION

As is well known to those skilled in the art, anhydrides of polycarboxylic acids, typified by the anhydride of maleic acid, are susceptible to deterioration when subjected to heat; and this deterioration is catalyzed by light and by chemical contaminants.

Polycarboxylic acid anhydrides including dicarboxylic acid anhydrides are subject to relatively high temperature environments in their manufacture, their purification, their use as chemical intermediates, and in cases of careless handling. These high temperatures cause deterioration which is evidenced by discoloration resulting from decomposition. Contamination can accelerate this thermal deterioration. In the case of the typical maleic anhydride, temperatures above 150° C. for extended periods of time can result in extensive even violent decomposition; the upward limit of applicability of stability additives has been stated (U.S. Pat. No. 3,636,057) to be ca. 180° C. due to decomposition or charring at this temperature.

The extent of deterioration and, therefore, the degree of protection required depends on the quality, method of production, feedstocks, conditions of handling and useful application as well as the nature and amount of stabilizer added and/or treatments given to the acid anhydrides to counteract this deterioration. In addition, deterioration requires definition.

Using maleic acid anhydride as an illustrative example (as it is one of the anhydrides particularly requiring thermal stabilization), thermal stability has been defined as a discoloring after 2 or more hours at 140° C. as measured by APHA (American Public Health Association) Units in accordance with ASTM-1209.

It is an object of this invention to provide a novel stabilized composition containing an anhydride of a polycarboxylic acid. Other objects will be apparent to those skilled in the art.

SUMMARY OF THE INVENTION

In accordance with certain of its aspects, this invention includes a composition stabilized against the deteriorative effect of heat comprising an anhydride of a polycarboxylic acid and as a stabilizer an inorganic boron-oxygen compound preferably selected from the group consisting of boric acid, borate salts, boric acid esters, metaboric acid, metaborate salts, metaboric acid esters, tetraborate salts, boron monoxide, and boric oxide.

DESCRIPTION OF THE INVENTION

The acid anhydrides which may be stabilized by the process of this invention may be mono-anhydrides or poly-anhydrides, including di-anhydrides, of polycarboxylic acids which form acid anhydrides. These acids may be saturated or unsaturated dicarboxylic acids, tricarboxylic acids, etc.

In one embodiment, the acid anhydrides may be anhydrides of acids of the formula $$R(COOH)_x \quad (I)$$

wherein R is a hydrocarbyl nucleus having at least one carbon atom and x is an integer greater than one. It will be apparent that R may be nomenclated based on the hydrocarbon from which it is derived; but hydrogen atoms thereon will be replaced as (i) by carboxyl groups which join together to form the anhydride ring—or (ii) by inert groups.

In the above formula (I), R may be a hydrocarbon radical selected from the group consisting of alkyl, aralkyl, cycloalkyl, aryl, alkaryl, alkenyl, and alkynyl including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, betaphenylethyl, etc. When R is cycloalkyl, it may typically be cyclopentyl, cyclohexyl, cycloheptyl, cyclooctyl, 2-methylcycloheptyl, 3-butylcyclohexyl, 3-methylcyclohexyl, etc. When R is aryl, it may typically be phenyl, naphthyl, etc. When R is alkaryl, it may typically be tolyl, xylyl, etc. When R is alkenyl, it may typically be vinyl, allyl, 1-butenyl, etc. When R is alkynyl, it may typically be ethynyl, propynyl, butynyl, etc. R may be inertly substituted i.e. it may bear a non-reactive substituent such as alkyl, aryl, cycloalkyl, ether, halogen, nitro, etc. Typically inertly substituted R groups may include 3-chloropropyl, 2-ethoxyethyl, carboethoxymethyl, 4-methyl cyclohexyl, p-chlorophenyl, p-chlorobenzyl, 3-chloro-5-methylphenyl, etc. The preferred R groups may be lower alkyl, i.e. $C_1$–$C_{10}$ alkyl, groups including eg methyl, ethyl, n-propyl, i-propyl, butyls, amyls, hexyls, octyls, decyls, etc. R may preferably be n-propyl.

In one embodiment of this invention, R of formula I may be $$C_nH_{(2n+2-x)} \quad (II)$$

wherein n is an integer of at least one.

In the formula, x may be an integer greater than 1, typically 2–6, say 2. If x be, eg 4, the acid may be inter alia, n-octane-1,2,4,6-tetracarboxylic acid
n-decane-1,2,3,4,-tetracarboxylic acid
n-heptane-4-phenyl-1,4,6,7-tetracarboxylic acid
n-pentane-3-ethyl-1,2,4,5-tetracarboxylic acid, etc.

If x be, eg 5, the acid may be, inter alia, n-pentane-3-(n-pentyl)-1,2,3,5,5-pentacarboxylic acid
n-decane-2,4,6-methyl-1,1,5,7,9-pentacarboxylic acid
n-nonane-5-phenyl-1,2,5,8,9-pentacarboxylic acid, etc.

In one embodiment of the invention, x of formula I may be 3 and the acid may be tricarboxylic acids such as:

n-butane-1,2,4,-tricarboxylic acid
n-pentane-1,2,3-tricarboxylic acid
n-pentane-1,3,5-tricarboxylic acid
n-pentane-1,3,3-tricarboxylic acid
n-butane-1,2,5-tricarboxylic acid
3-methyl-n-pentane-1,3,5-tricarboxylic acid
5-phenyl-n-pentane-1,3,5-tricarboxylic acid
n-nonane-1,5,9-tricarboxylic acid
n-nonane-1,2,3-tricarboxylic acid
5-methyl-nonane-1,5,9-tricarboxylic acid If the R of formula 1 contains four to six carbon atoms, the acid may be, for example, n-butane-1,2,3-tricarboxylic acid, n-pentane-2,3,4-tricarboxylic acid, n-hexane- 1,3,6-tricarboxylic acid. The acid may be n-pentane-1,3,5-tricarboxylic acid, (i.e. octric acid).

In the preferred embodiment, the anhydride may be a mono-anhydride of a dicarboxylic acid containing 2–6 carbon atoms e.g. in the above formulae, R may be a hydrocarbon containing 2–6 carbon atoms, x may be 2, and n may be 2.

Illustrative mono-anhydrides of dicarboxylic acids which may be used in practice of the process of this invention may be mono-anhydrides of the following acids:
malonic acid
succinic acid
glutaric acid
maleic acid
citraconic acid
phthalic acid For purpose of convenience, reference may be hereinafter made to maleic anhydride.

It is a feature of the process of this invention that the stabilizers may be used to stabilize substituted anhydrides of polycarboxylic acids, including for example reaction products of dicarboxylic acid anhydrides with alkenes (including polyalkenes) typified by alkenyl succinic anhydride of $\overline{M}_n$ of about 1000.

Stabilization of the anhydrides of polycarboxylic acids in accordance with practice of this invention may be effected by adding thereto a stabilizing amount of an inorganic boron-oxygen compound selected from the group consisting of boric acid, borate salts, boric acid esters, metaboric acid, metaborate salts, metaboric acid esters, tetraborate salts, boron monoxide, and boric oxide. A stabilizing amount, which is sufficient to stabilize the anhydride against the deteriorative effect of heat, may depend upon the conditions to which the anhydride is to be subjected. It may commonly be as low as 50 ppm (parts per million) up to 5 wt %. More typically it will be 0.1–2 w %, say 0.5–1%. It may be common to utilize the heat stabilizers of this invention in amount of about 1% of the acid anhydride.

In order to provide stability during manufacture of the anhydride, the stabilizer may be added with the feedstock (commonly the acid) prior to formation of the anhydride, or to the materials during processing as prior to heating or distillation where such steps are employed. When the additive is added during formation or processing or recovery, enough may be present to provide a stabilizing amount; or alternatively an additional quantity may be added to the finished product anhydrides.

When the stabilizer to be employed is a boric acid ester, it may be a mono-ester, a di-ester, or a tri-ester, typified by:
mono-methyl borate
di-methyl borate
tri-methyl borate
tri-ethyl borate
tri-propyl borate
tri-n-butyl borate
tri-secbutyl borate
2,6-di-t-butylphenyl, dibutyl borate
triphenyl borate Boric acid esters with polyols, such as ethylene glycol, may be employed.

It should be noted that the esters which are used in this invention (eg methyl borate) are nomenclated as inorganic boron-oxygen compounds because they do not possess a carbon-to-boron bond which is the characteristic of an organoboron compound.

When the stabilizer to be employed is metaboric acid, $HBO_2$, it may be available or it may be prepared by heating boric acid $H_3BO_3$ slowly as water is lost.

When the stabilizer to be employed is a metaborate salt, alkali metal metaborate salts may be useful. Typical of these may be $NaBO_2$ (also designated $Na_2B_2O_4$).

When the stabilizer to be employed is a metaborate acid ester, $RBO_2$, the preferred may be an alkyl, preferably a lower alkyl metaborate such as ethyl metaborate.

When the stabilizer to be employed is boric acid $H_3BO_3$, the boric acid of commerce may be employed. This is orthoboric acid $H_3BO_3$.

When the stabilizer to be employed is a borate salt, it may for example be $M^{+m}(B(OH)_4^-)_m$ or $M^{+m}(B_3O_3$-$(OH)_4)_m$ wherein M is a cation of charge + m. A preferred borate salt may be zinc triborate $Zn(B_2O_3(OH)_3)$ also known as tetrazinc dodecarborate heptahydrate.

When the stabilizer to be employed is a tetraborate salt, it may be an alkali salt such as the sodium or potassium salts. The preferred salt is borax sodium tetraborate $Na_2B_4O_7$, preferably in anhydrous form or as the decahydrate.

When the stabilizer to be employed is boron monoxide $(BO)_n$ or boric oxide $B_2O_3$, the forms of commerce may be employed.

It will be apparent to those skilled in the art that many of the noted boron compounds may be obtained in impure forms which include decomposition products or other boron compositions; and these are included within the scope of this invention. For example borax may be used in anhydrous form, as its pentahydrate, or as its decahydrate. Depending upon the conditions of formation and treatment, a borate may be converted to a metaborate or to a tetraborate. All of these may find use in practice of this invention whether pure or in admixture. Stabilization may also be effected by any of a wide group of inorganic boron-oxygen compounds identified by the formula

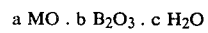

$$a\, MO \cdot b\, B_2O_3 \cdot c\, H_2O$$

wherein a and c may be zero or an integer and b may be an integer. In this nomenclature, for example sodium borate decahydrate (borax) may be designated $Na_2O.2$-$B_2O_3.10H_2O$.

Pure, commercial, or impure materials may be employed.

The preferred stabilizers to be employed include sodium tetraborate preferably as its decahydrate - $Na_2B_4O_7.10H_2O$ borax; tributyl borate $(C_4H_9O)_3B$; boric anhydride $B_2O_3$; and boric acid $H_3BO_3$.

Most preferred of these is boric acid which is characterized by its ready availability in high purity, moderate cost, and high effectivity as a stabilizing agent.

Stabilization is preferably effected by mixing or blending the boron compound with the superficially dry anhydride. Either one may be in a solution (aqueous or otherwise) when the two are mixed. It may however be possible (and in some instances desirable) to add the stabilizer to the anhydride (or to precursors thereof) as it is being formed or recovered.

The stabilized composition containing anhydride plus inorganic boron-oxygen composition is particularly characterized by its ability to resist darkening and discoloration when subjected to extended periods at high temperature .

In order to establish a reproducible scale by which the darkening of the typical maleic anhydride can be measured, arbitrary color standards were prepared from a sample of acetone-soluble maleic acid anhydride thermal degradation product and acetone. The thermal degradation product is a friable, brown-black solid believed to be a partially decarboxylated polymer of maleic acid anhydride. Table I below recites the concentration of this degradation product in acetone and the standard color scale for colorimetric comparisons. Other color scales are shown for reference.

| Standard Color No. | gram liter | COLOR SCALE ASTM Color D-1500 (range) | APHA Color D-1209 |
|---|---|---|---|
| 0 | none | 0.0 | — |
| 1 | 0.20 | L1.5–0.5 | >500 |
| 2 | 0.40 | L2.5–1.0 | — |
| 3 | 0.60 | 3.0–2.5 | — |
| 4 | 0.80 | 3.5–3.0 | — |
| 5 | 1.20 | 4.5–3.5 | — |
| 6 | 1.60 | L5.5–4.5 | — |
| 7 | 2.0 | 6.0–L5.5 | — |
| 8 | 2.8 | 7.5–6.0 | — |
| 9 | 4.0 | 8.0–7.5 | — |
| 10 | >10 | D 8.0 | — |

L - lighter than
D - darker than

The standard color scale is comparable to the range of colors in the D-1500 ASTM color scale, but the standard hues more closely match the hues of maleic acid anhydride as it decomposes, and these solutions enable work with small quantities of maleic acid anhydride. When the standard solutions are visually observed using transmitted light from two 15-watt daylight-type fluorescent lamps at close range in about 7 mm. high layers in about 18 mm OD, standard, 3-dram, clear glass vials, the standard no. 0 is clear and colorless, no. 1 is a very light yellow tint, no. 9 is a clear, deep reddish brown, nos. 2 through 8 are progressively and gradually less transmittant and more reddish-brown in hue in approximately equal steps between nos. 1 and 9, and no. 10 is an opaque, dark reddish brown. The maximum APHA color is not as dark as the standard no. 1 solution when viewed under the conditions of the APHA determination.

High Temperature Color Stability Test

In order to carry out the test, 1.0 gram of molten maleic acid anhydride (or other anhydride to be tested) (at a temperature above the melting point and less than 60° C. for no longer than 10 minutes) is placed in a standard 3-dram vial which is then sealed with a screw cap having a polymeric liner-seal. Using a stopwatch to gauge the time to within a few seconds, the vial is placed into a shallow oil bath heated to 199±3° C. for timed intervals in between which the vial is removed for a timed interval and rated for color by comparison with color rating scale standard at room temperature. If a color is obtained which appears to be between two adjacent color standards the rating assigned is exactly between these two standards, i.e., if the color to be matched appears to be between colors 4 and 5 and not 4 or 5, the rating assigned is 4.5.

In order to provide a simple index of performance (the Color Rating Index) in this test, the mean number of the heating interval over which the most color change occurs is used. In cases where there is no marked change or where there are other interferences with using this index, supplementary information is recorded. In general, the higher the index (heating interval where most pronounced color change occurs) and the lower the color rating after a given number of heating intervals, the better is the thermal stability. A rating of 10 for color indicates significant color generation signaling at least 1% deterioration of the mass of maleic acid anhydride. This decomposition is autocatalytic and it is believed that deterioration which has proceeded to this point signifies at least the onset of extensive degradation. At a APHA rating of 500 (the maximum), maleic acid anhydride is only slightly discolored and still consists of essentially all the maleic anhydride content it possessed before moderate heat treatment.

Because the conditions of this test could result in extensive decomposition, the vials are capped tightly enough to contain essentially all of the vapor, but loose enough to vent excessive pressure due to degradation. Safety devices should be used in performing this test.

Two heating interval protocols have been used. Both protocols call for 2 minute rating intervals. Protocol A calls for the first heating interval to be 2 minutes, the second heating interval to be 4 minutes, and the third and all subsequent heating intervals to be 3 minutes. Protocol B calls for all heating intervals to be 3 minutes. The heating intervals are discontinued after a rating of 10 is achieved or after a sufficient number of intervals has been carried out for the purposes of the test.

It is found that acid anhydrides stabilized by practice of this invention are generally characterized by a Color Rating Index of greater than three and frequently as high as 6–9. This means that little or no rapid color change has occurred at least up to the 6–9th period. In contrast, control runs frequently show a Color Rating Index of 1 i.e. show a very high degree of color change during the first period; and in fact the Standard Color No. is frequently above 7 after the second interval. Even the better controls show a Color Rating Index of 2–3.

It is of particular significance to note that Color Stability Test is carried out at a temperature (199° C.) which is substantially higher than the temperature (ca 180° C.) which has been set by the prior art as the maximum upper limit at which stability additives would be effective. The compositions of the instant invention are unexpectedly found to be effective in low concentrations at these high temperatures.

Specific illustrative compositions falling within the scope of this invention include the following:

(i) maleic anhydride (reagent grade); 50 ppm boric acid
(ii) maleic anhydride (commercial grade); 1 wt % boric acid
(iii) maleic anhydride (reagent grade); 0.5 wt % boric anhydride
(iv) succinic anhydride; 1 wt % borax decahydrate
(v) phthalic anhydride; 0.7 wt % tributylborate
(vi) citraconic anhydride; 0.5 wt % boric acid

DESCRIPTION OF PREFERRED EMBODIMENTS

Practice of the novel process of this invention may be apparent from the following description of preferred embodiments wherein, as elsewhere in this specification, all parts are parts by weight unless otherwise specifically noted.

EXAMPLES I*–II*

A pure reagent grade of maleic anhydride (Example I) which contains no known additives (Aldrich Chemical Co. Catalog No. M18-8) (analyzed by proton NMR spectroscopy to be about 99 mole % maleic anhydride and about 1% maleic acid) and a commercial grade of maleic anhydride (Example II) which is believed to contain a proprietary, thermal stability additive (Petrotex briquettes) (mp 52°–53° C.) were tested in the High Temperature Color Stability Test with the results shown below:

| | Protocol A | | | | | | |
|---|---|---|---|---|---|---|---|
| Elapsed time (min) | 0–2 | 4–8 | 10–13 | 15–18 | 20–23 | 25–28 | |
| Heating Interval No. | 1 | 2 | 3 | 4 | 5 | 6 | Mean Index |
| Additive-free Maleic Anhydride Example I Standard Color | 0.5 | 8.2 | 9.7 | 10 | | | 1.0 |
| Commercial Grade Maleic Anhydride Example II Standard Color (Mean) | 0.5 | 2.4 | 7.1 | 9.5 | 10 | | 2.5 |

| | Protocol B | | | | | | |
|---|---|---|---|---|---|---|---|
| Elapsed time (min) | 0–3 | 5–8 | 10–13 | 15–18 | 20–23 | 25–28 | |
| Heating Interval No. | 1 | 2 | 3 | 4 | 5 | 6 | |
| Example I Standard Color (Mean) | 0.5 | 3.9 | 7.1 | 9.2 | 9.7 | 10.0 | 2.2 |
| Example II Standard Color (Mean) | 0.5 | 1.5 | 3.3 | 5.9 | 8.8 | 9.7 | 3.5 |

Standard Color

| | | Protocol A | | | | | | |
|---|---|---|---|---|---|---|---|---|
| Examples | Heating Interval: Additive | 1 | 2 | 3 | 4 | 5 | 6 | Index |
| III* | mono-t-butylhydroquinone | 2.5 | 7.5 | 9.5 | 10 | | | 1 |
| IV* | 1,1-thio bis(2-naphthol) | 10 | | | | | | 1 |
| V* | ethylene diamine tetraacetic acid di sodium salt | 10 | | | | | | 1 |
| VI* | ethylene diamine tetraacetic acid | 4.5 | 10 | | | | | 1 |
| VII* | dithiopropionic acid | 0.5 | 7 | 9 | 9.5 | 9.5 | 10 | 1 |
| VIII* | 4-t-butylcatechol | 0.5 | 7 | 9.5 | 9.5 | 10 | | 1 |
| IX* | ascorbic acid | 6.5 | 9 | 9.5 | 9.5 | 10 | | 1 |
| X* | hydroquinone | 0.5 | 7.5 | 9.5 | 10 | | | 1 |
| XI* | propyl gallate | 0.5 | 9.5 | 10 | | | | 1 |
| XII* | 2-t-butyl-4-hydroxyanisole | 2.5 | 8 | 9.5 | 10 | | | 1 |
| XIII* | 2,6-di-t-butyl-p-cresol | 0.5 | 9.5 | 9.5 | 10 | | | 1 |
| XIV* | p-acetophenetidide | 0.5 | 9.5 | 10 | | | | 1 |

| | | Protocol B | | | | | | |
|---|---|---|---|---|---|---|---|---|
| Examples | Heating Interval: Additive | 1 | 2 | 3 | 4 | 5 | 6 | Index |
| XV* | zirconium oxychloride | 0.5 | 2.5 | 7.5 | 9.5 | 9.5 | 9.5 | 2.5 |
| XVI* | tri-o-tolyl thiophosphate | 0.5 | 2.5 | 5.5 | 8.5 | 9.5 | 9.5 | 3 |
| XVII* | tri-o-tolyl thiophosphate | 0.5 | 3.5 | 7.5 | 9.5 | 9.5 | 9.5 | 2 |
| XVIII* | tri-p-cresyl phosphate | 0.5 | 2.5 | 6.5 | 9.5 | 9.5 | 9.5 | 3 |
| XIX* | arsenic trichloride | 0.5 | 7.5 | 9.5 | 9.5 | 9.5 | 9.5 | 1 |
| XX* | vanadium acetylacetonate | 2.5 | 7.5 | 9.5 | 9.5 | 10 | | 1 |
| XXI* | cobalt(II) acetylacetonate | 3 | 7.5 | 9.5 | 9.5 | 10 | | 1 |
| XXII* | triethyl phosphorothioate | 0.5 | 2.5 | 5.5 | 7.5 | 8 | 9.5 | 3 |
| XXIII* | aluminum trichloride | 0.5 | 1.5 | 4 | 7.5 | 9.5 | 9.5 | 3 |

| | | | Heating Interval | | | | | | | | | |
|---|---|---|---|---|---|---|---|---|---|---|---|---|
| Examples | Additive | Protocol | 1 | 2 | 3 | 4 | 5 | 6 | 7 | 8 | 9 | Index |
| XXIV | boric acid | A | 0.5 | → | → | → | → | → | → | → | 0.5 | >9 |
| XXV | boric anhydride | B | 0.5 | 0.5 | 0.5 | 0.5 | 0.5 | 1 | | | | >6 |
| XXVI | boric anhydride | B | 0.5 | 0.5 | 0.5 | 1 | 1 | 1 | | | | >6 |
| XXVII | tributylborate | B | 0.5 | 0.5 | 0.5 | 1 | 2 | 2 | | | | >6 |
| XXVIII | borax | B | 0.5 | 1.5 | 4.5 | 4.5 | 6.5 | 6.5 | | | | >3 |

Results comparable to the above may be attained when the anhydride is:

| Example | Anhydride |
|---|---|
| XXIX | succinic anhydride |
| XXX | malonic anhydride |
| XXXI | citraconic anhydride |

-continued

| Example | Anhydride |
| --- | --- |
| XXXII | phthalic anhydride |
| XXXIII | polyisobutenyl succinic anhydride of $M_n$ of ca 1000 |

The stabilized anhydride compositions of this invention may find use in a wide variety of applications. For example maleic anhydride, stabilized with boric acid, may be reacted with olefin polymers to form additives for lubricating oils (as in U.S. Pat. No. 3,018,250), reacted with butyl rubber to form modified rubber (as in U.S. Pat. No. 2,845,403), etc.

Although this invention has been illustrated by reference to specific embodiments, it will be apparent to those skilled in the art that various changes and modifications may be made which clearly fall within the scope of this invention.

I claim:

1. A composition stabilized against the deteriorative effect of heat comprising an anhydride of a polycarboxylic acid and as a stabilizer an inorganic boron-oxygen compound.

2. A composition stabilized against the deteriorative effect of heat as claimed in claim 1 wherein said boron-oxygen compound is boric acid $H_3BO_3$.

3. A composition stabilized against the deteriorative effect of heat as claimed in claim 1 wherein said boron-oxygen compound is a borate salt.

4. A composition stabilized against the deteriorative effect of heat as claimed in claim 1 wherein said boron-oxygen compound is a boric acid ester $B(OR)_3$ wherein R is selected from the group consisting of hydrogen, alkyl, aryl, alkaryl, aralkyl, cycloalkyl, at least one of said R groups being other than hydrogen.

5. A composition stabilized against the deteriorative effect of heat as claimed in claim 1 wherein said boron-oxygen compound is a boric acid ester $B(OR)_3$ wherein R is a $C_1$ to $C_{10}$ lower alkyl group.

6. A composition stabilized against the deteriorative effect of heat as claimed in claim 1 wherein said boron-oxygen compound is metaboric acid.

7. A composition stabilized against the deteriorative effect of heat as claimed in claim 1 wherein said boron-oxygen compound is a metaboric acid ester.

8. A composition stabilized against the deteriorative effect of heat as claimed in claim 1 wherein said boron-oxygen compound is a tetraborate salt.

9. A composition stabilized against the deteriorative effect of heat as claimed in claim 1 wherein said boron-oxygen compound is sodium tetraborate $Na_2B_4O_7$.

10. A composition stabilized against the deteriorative effect of heat as claimed in claim 1 wherein said boron-oxygen compound is boron monoxide.

11. A composition stabilized against the deteriorative effect of heat as claimed in claim 1 wherein said boron-oxygen compound is boric oxide.

12. A composition stabilized against the deteriorative effect of heat as claimed in claim 1 wherein said anhydride of a polycarboxylic acid is maleic anhydride.

13. A composition stabilized against the deteriorative effect of heat as claimed in claim 1 wherein said anhydride of a polycarboxylic acid in succinic anhydride.

14. A composition stabilized against the deteriorative effect of heat as claimed in claim 1 wherein said anhydride of a polycarboxylic acid is phthalic anhydride.

15. A composition stabilized against the deteriorative effect of heat as claimed in claim 1 wherein said anhydride of a polycarboxylic acid is citraconic anhydride.

16. A composition stabilized against the deteriorative effect of heat comprising an anhydride of a dicarboxylic acid and as a stabilizer an inorganic boron-oxygen compound selected from the group consisting of boric acid, borate salts, boric acid esters, metaboric acid, metaborate salts, metaboric acid esters, tetraborate salts, boron monoxide, and boric oxide.

17. A composition stabilized against the deteriorative effect of heat comprising maleic anhydride and a stabilizing amount of 50 ppm - 5 wt % of boric acid $H_3BO_3$, boric anhydride $B_2O_3$, tributyl borate $B(OC_4H_9)_3$, or borax $Na_2B_4O_7$.

18. The method of stabilizing an anhydride of a polycarboxylic acid against the deteriorative effect of heat which comprises adding to an anhydride of a polycarboxylic acid an inorganic boron-oxide compound as a stabilizer thereby stabilizing said anhydride of said polycarboxylic acid against the deteriorative effect of heat; and recovering stabilized anhydride of a polycarboxylic acid containing said boron-oxide compound as a stabilizer.

19. The method of stabilizing maleic anhydride against the deteriorative effect of heat which comprises adding to maleic anhydride an inorganic boron-oxide compound as a stabilizer thereby stabilizing said anhydride against the deteriorative effect of heat; and recovering stabilized maleic anhydride containing said inorganic boron-oxide compound as a stabilizer.

20. A composition stabilized against the deteriorative effect of heat comprising an alkenyl succinic anhydride and as stabilizer an inorganic boron-oxygen compound.

21. A composition stabilized against the deteriorative effect of heat as claimed in claim 20 wherein said alkenyl succinic anhydride is polyisobutenyl succinic anhydride.

22. A composition stabilized against the deteriorative effect of heat as claimed in claim 20 wherein said inorganic boron-oxygen compound is present in amount of 50 ppm - 5w %.

* * * * *

UNITED STATES PATENT AND TRADEMARK OFFICE
CERTIFICATE OF CORRECTION

PATENT NO. : 4,257,958
DATED : March 24, 1981
INVENTOR(S) : J. C. Powell

It is certified that error appears in the above-identified patent and that said Letters Patent are hereby corrected as shown below:

In the Abstract, line 4, correct the spelling of "tributyl";

Claim 13, line 3, cancel "in", insert -- is --.

Signed and Sealed this

First Day of September 1981

[SEAL]

Attest:

GERALD J. MOSSINGHOFF

Attesting Officer

Commissioner of Patents and Trademarks